United States Patent [19]

Kempe et al.

[11] Patent Number: 4,658,035
[45] Date of Patent: Apr. 14, 1987

[54] PREPARATION OF 2-ALKYL-4,5-DIHYDROXYME-THYLIMIDAZOLES

[75] Inventors: Uwe Kempe, Dannstadt-Schauernheim; Toni Dockner, Meckenheim, both of Fed. Rep. of Germany

[73] Assignee: BASF Aktiengesellschaft, Ludwigshafen, Fed. Rep. of Germany

[21] Appl. No.: 754,852

[22] Filed: Jul. 12, 1985

[30] Foreign Application Priority Data

Jul. 14, 1984 [DE] Fed. Rep. of Germany ........ 3426081

[51] Int. Cl.$^4$ .......................................... C07D 233/64
[52] U.S. Cl. .................................................... 548/342
[58] Field of Search .......................................... 548/342

[56] References Cited

U.S. PATENT DOCUMENTS 4,104,473 8/1978 Sawa et al. ................ 548/342
4,189,591 2/1980 Mueller et al. ............ 548/342
4,278,801 7/1981 Kempe et al. ............. 548/342

OTHER PUBLICATIONS

E. F. Godefroi, et al., 91 (1972), *Recueil*, pp. 1383–1392.
M. Masui, et al., *Chem. Pharm. Bulletin*, 22 (10), pp. 2359–2364.

*Primary Examiner*—Richard A. Schwartz
*Attorney, Agent, or Firm*—John H. Shurtleff

[57] ABSTRACT

2-Alkyl-4,5-dihydroxymethyl-imidazoles of the formula

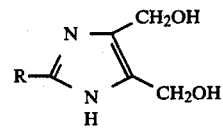

where R is alkyl, are prepared by a process in which an imidazole of the formula

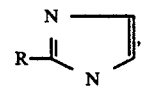

is reacted with not less than 2 moles of formaldehyde in the presence of a base.

8 Claims, No Drawings

PREPARATION OF 2-ALKYL-4,5-DIHYDROXYMETHYLIMIDAZOLES

The present invention relates to a process for the preparation of 2-alkyl-4,5-dihydroxymethylimidazoles by reacting a 2-alkylimidazole with formaldehyde.

2-Alkyl-4,5-dihydroxymethylimidazoles are desirable intermediates for the preparation of dyes and active ingredients, and are prepared by, for example, reduction of the corresponding imidazolecarboxylic acids. Monohydroxymethylimidazoles, such as 4-methyl-5-hydroxymethylimidazole, which is a known intermediate for drugs, are obtained, for example, in accordance with European Pat. No. 4,534, by reacting 4-methylimidazole with formaldehyde in an alkaline medium. Furthermore, 4,5-dihydroxymethylimidazoles which contain aryl groups in the 2-position have been prepared by treating the corresponding 2-arylimidazoles with formaldehyde. This process, described in German Laid-Open Application DOS No. 2,618,756, is preferably carried out in an aqueous medium at a pH of not less than 7. It is pointed out that the reaction of imidazoles which do not contain an aryl group in the 2-position with formaldehyde gives unstable 1-hydroxymethylimidazoles (cf. page 6, lines 8 to 13).

We have ound that 2-alkyl-4,5-dihydroxymethylimidazoles of the formula

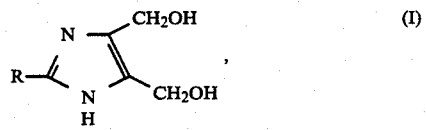

where R is alkyl of 1 to 17 carbon atoms which may furthermore contain radicals of the formula R'O—, R'$_2$N— or R'S—, and R' is alkyl of 1 to 4 carbon atoms, can be particularly advantageously prepared if an imidazole of the formula

where R has the above meanings, is reacted with not less than 2 moles of formaldehyde in the presence of a base.

The novel process gives the 2-alkyl-4,5-dihydroxymethylimidazoles in good yield. This advantageous result is very surprising since, on the basis of the information in German Laid-Open Application DOS No. 2,618,756 concerning the reaction characteristics of imidazoles, it was not to be expected that 2-alkylimidazoles could be reacted with formaldehyde under basic conditions to give 2-alkyl-4,5-dihydroxymethylimidazoles.

The imidazoles of the formula II which are suitable as starting materials contain an alkyl radical of 1 to 17 carbon atoms, such as methyl, ethyl, propyl, butyl or heptadecyl, in the 2-position. The alkyl radical may furthermore be substituted by alkyl ether, alkyl thioether or dialkylamino groups in which the alkyl radicals are of, for example, 1 to 4 carbon atoms. Examples of 2-alkylimidazoles are 2-methylimidazole, 2-ethylimidazole and 2-isopropylimidazole.

Not less than 2, preferably from 2 to 3, moles of formaldehyde are reacted per mole of 2-alkylimidazole. The formaldehyde is used, for example, in the form of paraformaldehyde, trioxane or an aqueous formaldehyde solution, advantageously as industrial aqueous solutions having formaldehyde contents of from 10 to 30% by weight. Methanol, which is present in industrial formaldehyde solutions, does not present problems. In the process according to the invention, the reaction of the imidazoles with the formaldehyde is carried out in the presence of a base, the pH of the reaction mixture being not less than 7, preferably from 7 to 13. The reaction temperatures are from 40° to 180° C., and the reaction pressure is not critical.

Examples of suitable bases are the hydroxides of the alkali metals or alkaline earth metals, such as NaOH or KOH. The bases used may furthermore be tertiary amines, such as triethylamine, tri-n-butylamine or methyldibutylamine. The base, which acts as a catalyst, is employed in amounts of, for example, from 0.1 to 1.0, preferably from 0.3 to 0.7, mole per mole of imidazole. Where alkali metal or alkaline earth metal hydroxides are used, the pH initially established is kept constant by adding further amounts of the base.

When the reaction is complete, which takes about 20–60 hours, the dimethylol compounds are isolated from the reaction mixture, for example after distilling off the volatile components. A particular industrial advantage of this process is that the volatile tertiary amines can be reused.

The 2-alkyl-4,5-dihydroxymethylimidazoles obtainable by the process of the invention are useful intermediates for dyes, plastics and specialty chemicals. The Examples which follow illustrate the invention without restricting it. The compounds obtained were identified by nuclear magnetic resonance and elemental analysis, as stated below.

EXAMPLE 1

2-Methyl-4,5-dihydroxymethylimidazole 82 g (1 mole) of 2-methylimidazole and 220 g (2.2 moles) of 30% strength by weight aqueous formaldehyde solution are stirred for 1 hour at 60° C., 50.4 g (0.49 mole) of triethylamine are added to the mixture, and stirring is continued for 48 hours under reflux at about 78° C. The solution is evaporated to dryness under reduced pressure at a bath temperature of 60° C., 160 g of crude product being obtained during this procedure. The crude product is stirred with 128 g of methanol and 32 g of isopropanol, for 30 minutes in each case, at 50° C. and at 10° C. with cooling. The colorless solid is then filtered off, washed with twice 200 ml of acetone and dried for 12 minutes at 45° C. to give 91.6 g of 2-methyl-4,5-dihydroxymethylimidazole of melting point 182°–182.5° C. This corresponds to a yield of 64.5%. The purity (HPLC) is 99.8%.

Elemental analysis:

|  | C | H | N | O |
|---|---|---|---|---|
| calculated | 50.7 | 7.1 | 19.7 | 22.5% |
| found | 50.6 | 7.6 | 19.7 | 22.1% |

Mass spectrum: M+142.

$^1$H-NMR spectrum (solvent DDMSO; TMS as internal standard, data in ppm): 2.18 (s, 3p) 4.35 (s, 4p).

EXAMPLE 2

2-Ethyl-4,5-dihydroxymethylimidazole

The procedure described in Example 1 is followed, except that 96 g (1 mole) of 2-ethylimidazole are used instead of 2-methylimidazole. The 155 g of crude product obtained in this procedure are stirred with 52 g of methanol for 30 minutes at 50° C. and at 10° C. with cooling. The mixture is filtered, the product is washed with twice 150 ml of acetone and dried in a drying oven, and 117.5 g of 2-ethyl-4,5-dihydroxymethylimidazole of melting point 173.35°–174.0° C. are obtained. This corresponds to a yield of 75.4%. The purity of this sample is 99.8% according to HPLC.

Elemental analysis:

|  | C | H | N | O |
|---|---|---|---|---|
| calculated | 53.9 | 7.7 | 17.9 | 20.5% |
| found | 54.0 | 7.8 | 17.7 | 20.5% |

Mass spectrum: M+156.

$^1$H-NMR spectrum (solvent DDMSO) 1.15 (t, 1p) 2.55 (q, 2p) 4.4 (s, 4p).

EXAMPLE 3

2-Isopropyl-4,5-dihydroxymethylimidazole 110 g (1 mole) of 2-isopropylimidazole and 220 g (2.2 moles) of a 30% strength aqueous formaldehyde solution are stirred for 1 hour at 60° C., 50.4 g (0.44 mole) of triethylamine are added to the mixture, and stirring is continued under reflux at about 78° C. The product crystallizes out from the mixture. After 48 hours, the mixture is cooled to 5° C. After 1 hour, the product is isolated by filtration. 136.8 g of crude product are obtained, and this is washed with twice 200 ml of acetone and dried in a drying oven under reduced pressure at 450° C. to give 126.1 g of 2-isopropyl-4,5-dihydroxymethylimidazole of melting point 199.5°–201.0° C. Evaporating down the filtrate gives 107 g of a crude product from which a further 18.5 g of 2-isopropyl-4,5-dihydroxymethylimidazole can be obtained by stirring with 107 g of methanol at 50° C. for 30 minutes and then cooling at 5° C. for 30 minutes, filtering and drying. The total yield is 84.8%.

Elemental analysis:

|  | C | H | N | O |
|---|---|---|---|---|
| calculated | 56.5 | 8.2 | 16.5 | 18.8% |
| found | 56.7 | 8.6 | 16.5 | 18.2% |

Mass spectrum: M+170.

$^1$H-NMR spectrum (solvent DDMSO): 1.12 1.24 (d, 6p) 2.9 (septet, 1p) 4.35 (s, 4p).

EXAMPLE 4

2-Ethyl-4,5-dihydroxymethylimidazole

The procedure described in Example 2 is followed, except that 90.7 g (0.49 mole) of tri-n-butylamine are used instead of triethylamine. After 46 hours, 10 g of formaldehyde (in the form of a 30% strength aqueous solution) are added and, after a total of 62 hours at 110° C., the upper phase is separated off and the product is isolated by evaporation. The working-up procedure described in Example 2 gives 139.2 g of 2-ethyl-4,5-dihydroxymethylimidazole of melting point 173°–174° C. (yield 89.1%).

EXAMPLE 5

2-Methyl-4,5-dihydroxymethylimidazole 41 g of 2-methylimidazole are dissolved in 20 ml of water, 100 g of a 30% strength aqueous formaldehyde solution are added slowly to the solution at from 15° to 25° C., and the pH is brought to 12.4 with 9 ml of a 40% strength aqueous potassium hydroxide solution. The pH is kept at 12.4 during the reaction by adding a solution of potassium hydroxide and aqueous formaldehyde (molar ratio 1:2). After 28 hours, the mixture is evaporated down and the crude product is treated as described in Example 1. 55.7 g (yield 78.4%) of 2-methyl-4,5-dihydroxymethylimidazole of melting point 182°–182.5° C. are obtained.

The procedure described in the first paragraph is followed, except that 8 ml of a 40% strength sodium hydroxide solution are added instead of the potassium hydroxide solution, the pH thus being brought to 12.1. After 28 hours, the mixture is evaporated down, and the residue is worked up as described in Example 1. 50 g (yield 70.2%) of 2-methyl-4,5-dihydroxymethylimidazole of melting point 182°–182.5° C. are obtained.

We claim:

1. A process for the preparation of a 2-alkyl-4,5-dihydroxymethylimidazole of the formula

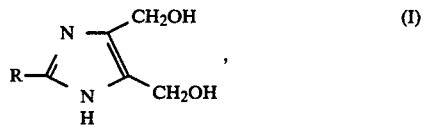

where R is alkyl of 1 to 17 carbon atoms which may furthermore contain radicals of the formula R'O—, R'$_2$N— or R'S—, and R' is alkyl of 1 to 4 carbon atoms, wherein an imidazole of the formula

where R has the above meanings, is reacted with not less than 2 moles of formaldehyde at from 40° to 180° C. in the presence of a tertiary amine.

2. A process as claimed in claim 1, wherein the reaction is carried out in an aqueous solution of the formaldehyde.

3. A process as claimed in claim 1, wherein the tertiary amine is used in an amount of from 0.1 to 1 mole per mole of imidazole.

4. A process as claimed in claim 1, wherein the tertiary amine is selected from the group consisting of triethylamine, tri-n-butylamine and methyldibutylamine.

5. A process as claimed in claim 4, wherein the tertiary amine is used in an amount of from 0.1 to 1 mole per mole of imidazole.

6. A process as claimed in claim 5, wherein the reaction is carried out in an aqueous solution of the formaldehyde.

7. A process as claimed in claim 4, wherein the tertiary amine is used in an amount of from 0.3 to 0.7 mole per mole of imidazle.

8. A process as claimed in claim 7, wherein the reaction is carried out in an aqueous solution of the formaldehyde.